US008845736B2

(12) United States Patent
Zhang et al.

(10) Patent No.: US 8,845,736 B2
(45) Date of Patent: *Sep. 30, 2014

(54) COMPOSITE IMPLANT

(71) Applicant: Zimmer Spine, Inc., Minneapolis, MN (US)

(72) Inventors: Kai Zhang, Woodbury, MN (US); Christopher J. Valois, Champlin, MN (US); Zhibin Fang, Eden Prairie, MN (US); Jeffrey A. Bassett, Vista, CA (US); Steven A. Zawadzki, Edina, MN (US); David C. Kirt, Minnetonka, MA (US); Steven E. Spangle, Bloomington, MN (US)

(73) Assignee: Zimmer Spine, Inc., Minneapolis, MN (US)

( * ) Notice: Subject to any disclaimer, the term of this patent is extended or adjusted under 35 U.S.C. 154(b) by 3 days.

This patent is subject to a terminal disclaimer.

(21) Appl. No.: 13/871,295

(22) Filed: Apr. 26, 2013

(65) Prior Publication Data

US 2013/0218280 A1   Aug. 22, 2013

Related U.S. Application Data

(63) Continuation of application No. 13/719,295, filed on Dec. 19, 2012, now Pat. No. 8,470,042, which is a continuation of application No. 12/829,979, filed on Jul. 2, 2010, now Pat. No. 8,361,150.

(60) Provisional application No. 61/245,115, filed on Sep. 23, 2009.

(51) Int. Cl.
*A61F 2/44* (2006.01)
*B32B 15/08* (2006.01)
*A61F 2/30* (2006.01)

(52) U.S. Cl.
CPC ............ *A61F 2/4465* (2013.01); *A61F 2/447* (2013.01); *A61F 2250/0046* (2013.01); *A61F 2250/0023* (2013.01); *A61F 2002/30044* (2013.01); *A61F 2002/30011* (2013.01); *A61F 2310/00131* (2013.01); *A61F 2250/0032* (2013.01); *B32B 15/08* (2013.01); *A61F 2/442* (2013.01); *A61F 2002/30971* (2013.01); *A61F 2002/30056* (2013.01)
USPC .................................. 623/17.16; 623/17.11

(58) Field of Classification Search
CPC ............ A61F 2/442; A61F 2002/2817; A61F 2002/3093; A61F 2002/30004; A61F 2002/30011
USPC .............. 606/246–249, 279; 623/17.11–17.16
See application file for complete search history.

(56) References Cited

U.S. PATENT DOCUMENTS 5,011,497 A   4/1991   Persson
(Continued)

FOREIGN PATENT DOCUMENTS

CN   1816309 A   8/2006
(Continued)

*Primary Examiner* — Pedro Philogene
*Assistant Examiner* — Christina Negrellirodrigue
(74) *Attorney, Agent, or Firm* — Seager, Tufte & Wickhem LLC

(57) ABSTRACT

A composite interbody vertebral implant for facilitating fusion of adjacent vertebrae. The implant includes a first endplate of a porous metal material and a second endplate of a porous metal material which are configured to allow bone in-growth. The implant also includes a polymeric body positioned between and bonded to the first and second endplates such that polymeric material of the polymeric body is impregnated into pores of the first and second endplates to bond the components together. The implant may include a cavity extending through the composite implant configured to receive bone growth material to facilitate fusion between a first vertebra and a second vertebra.

20 Claims, 14 Drawing Sheets

(56) References Cited

U.S. PATENT DOCUMENTS

| | | | |
|---|---|---|---|
| 5,071,437 A | 12/1991 | Steffee | |
| 5,282,861 A | 2/1994 | Kaplan | |
| 5,443,512 A | 8/1995 | Parr et al. | |
| 5,443,515 A | 8/1995 | Cohen | |
| 5,458,643 A | 10/1995 | Oka et al. | |
| 6,063,442 A | 5/2000 | Cohen | |
| 6,087,553 A | 7/2000 | Cohen et al. | |
| 6,258,125 B1 | 7/2001 | Paul et al. | |
| 6,533,818 B1 * | 3/2003 | Weber et al. | 623/17.16 |
| 6,554,863 B2 | 4/2003 | Paul et al. | |
| 6,726,720 B2 | 4/2004 | Ross et al. | |
| 7,192,447 B2 | 3/2007 | Rhoda | |
| 8,470,042 B2 * | 6/2013 | Zhang et al. | 623/17.11 |
| 2001/0016773 A1 | 8/2001 | Serhan et al. | |
| 2005/0100578 A1 | 5/2005 | Schmid et al. | |
| 2006/0121084 A1 | 6/2006 | Borden et al. | |
| 2006/0173542 A1 * | 8/2006 | Shikinami | 623/14.12 |
| 2006/0178749 A1 | 8/2006 | Pendleton et al. | |
| 2007/0055373 A1 | 3/2007 | Hudgins et al. | |
| 2007/0255412 A1 | 11/2007 | Hajaj et al. | |
| 2008/0161927 A1 * | 7/2008 | Savage et al. | 623/17.16 |
| 2008/0306609 A1 | 12/2008 | Lee et al. | |
| 2009/0030521 A1 | 1/2009 | Lee et al. | |

FOREIGN PATENT DOCUMENTS

| | | |
|---|---|---|
| CN | 1882294 A | 12/2006 |
| CN | 101137340 A | 3/2008 |
| EP | 0356112 A1 | 2/1990 |
| EP | 0392076 A1 | 10/1990 |
| WO | 8903663 A1 | 5/1989 |
| WO | 2005047467 A2 | 5/2005 |
| WO | 2006078662 A1 | 7/2006 |
| WO | 2007123861 A2 | 11/2007 |
| WO | 2008034276 A2 | 3/2008 |
| WO | 2009099559 A2 | 8/2009 |

* cited by examiner

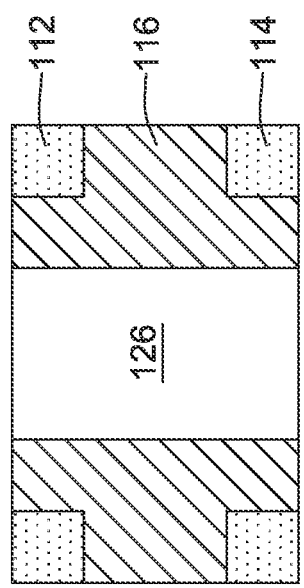
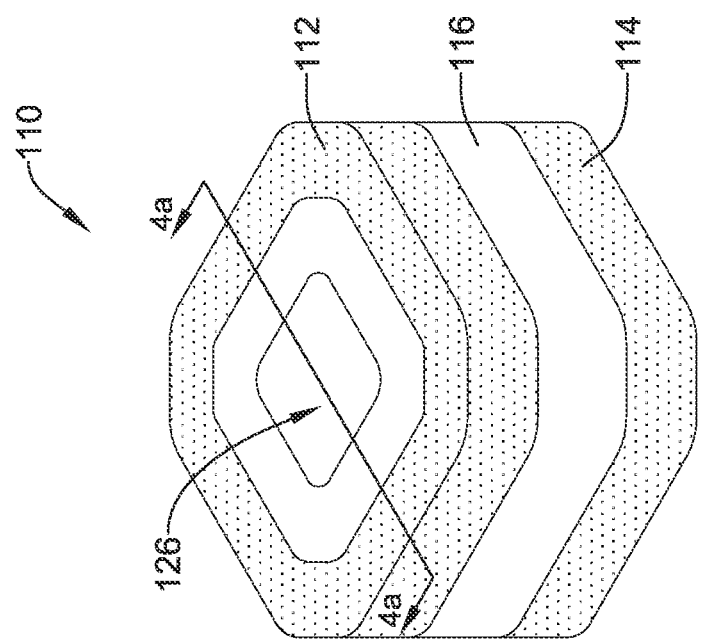

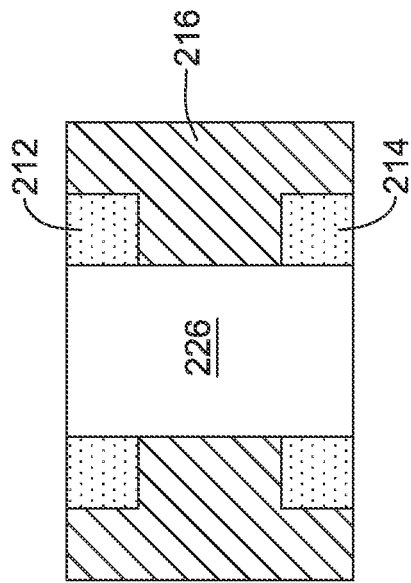
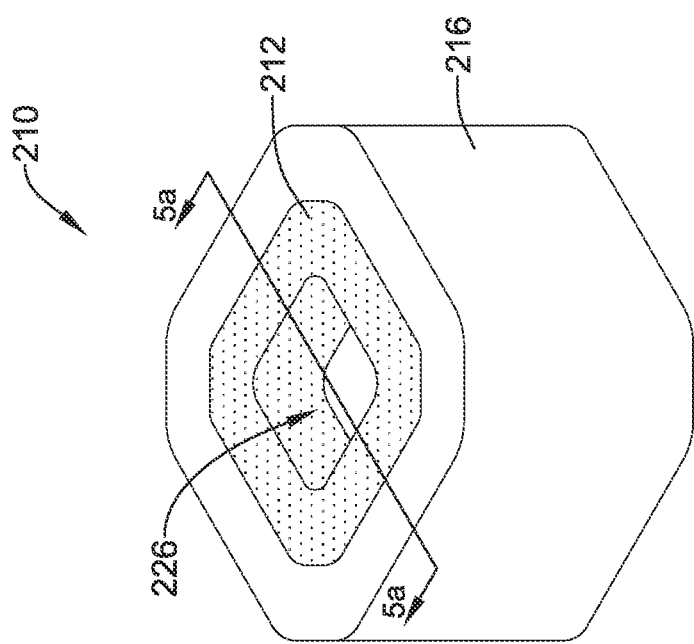
Figure 5A
Figure 5

COMPOSITE IMPLANT

CROSS-REFERENCE TO RELATED APPLICATIONS

This application is a continuation of U.S. patent application Ser. No. 13/719,295, filed Dec. 19, 2012, which is a continuation of U.S. patent application Ser. No. 12/829,979, filed Jul. 2, 2010, now U.S. Pat. No. 8,361,150, which claims priority to U.S. Provisional Application No. 61/245,115, filed on Sep. 23, 2009, the entire contents of which are incorporated herein by reference.

TECHNICAL FIELD

The disclosure is directed to composite implants for insertion between adjacent vertebrae. More particularly, the disclosure is directed to composite interbody vertebral implants formed of joined layers of porous metal bodies and one or more polymeric bodies, and methods of forming the same.

BACKGROUND

Chronic back problems cause pain and disability for a large segment of the population. Frequently, the cause of back pain is traceable to diseased or degenerated disc material between adjacent vertebrae. When the disc material is diseased, the adjacent vertebrae may be inadequately supported, resulting in persistent pain. Surgical techniques have been developed to remove all or part of the diseased disc material and fuse the joint between adjacent vertebral bodies. Stabilization and/or arthrodesis of the intervertebral joint can reduce the pain associated with movement of a diseased intervertebral joint. Spinal fusion may be indicated to provide stabilization of the spinal column for a wide variety of spine disorders including, for example, structural deformity, traumatic instability, degenerative instability, post-resection iatrogenic instability, etc.

Generally, fusion techniques involve partial or complete removal of the diseased disc and implanting a vertebral implant or spacer between the adjacent vertebral bodies to facilitate new bone growth between the vertebrae. The surface area, configuration, orientation, surface texture and deformity characteristics of an interbody spacer or bone graft placed in the disc space can affect the stability of the joint during fusion and thus affect the overall success of a fusion procedure.

Interbody spacers formed of stainless steel, titanium or titanium alloys, porous tantalum, and other biocompatible metal alloys are known. Furthermore, interbody spacers formed of polymeric materials such as polyether ether ketone (PEEK) are also known. With interbody implants made out of metal, the metal prevents adequate radiographic visualization of bone growth through the implant between the vertebrae. Dissimilarly, interbody implants made of a radiolucent material, such as polyetheretherketone (PEEK), may allow postoperative visualization of bone growth or fusion through the implant with an imaging device, such as on an X-ray.

In accordance with the present disclosure, composite implants are disclosed that can be inserted at a fusion site which may provide an osteoconductive scaffold for bony ingrowth while allowing post-operative visualization of bone growth or fusion through the implant using radiographic visualization instrumentation. Methods of manufacturing the composite implants are also disclosed.

SUMMARY

The disclosure is directed to several alternative designs, materials and methods of manufacturing composite interbody implants.

Accordingly, one illustrative embodiment is a composite interbody vertebral implant for facilitating fusion of adjacent vertebrae. The composite interbody vertebral implant includes a first body of porous metal, a second body of porous metal, and a polymeric body of a thermoplastic polymeric material positioned between the first body of porous metal and the second body of porous metal. The first body of porous metal defines a plurality of pores formed by a metallic scaffold configured to allow bone in-growth from a first vertebra. The second body of porous metal defines a plurality of pores formed by a metallic scaffold configured to allow bone in-growth from a second vertebra. A first interface layer located between the first body of porous metal and the polymeric body includes the polymeric material impregnated into the pores of the first body of porous metal. A second interface layer located between the second body of porous material and the polymeric body includes the polymeric material impregnated into the pores of the second body of porous metal. A cavity configured to receive bone growth material to facilitate fusion between the first vertebra and the second vertebra extends through the composite interbody vertebral implant.

Another illustrative embodiment is a composite interbody vertebral implant for facilitating fusion of adjacent vertebrae. The composite interbody vertebral implant includes a first body of a porous tantalum metal, a second body of a porous tantalum metal, and a polymeric body of polyether ether ketone (PEEK) positioned between the first body of porous tantalum metal and the second body of porous tantalum metal. The first body of porous tantalum metal defines a plurality of pores formed by a metallic scaffold configured to allow bone in-growth from a first vertebra. The second body of porous tantalum metal defines a plurality of pores formed by a metallic scaffold configured to allow bone in-growth from a second vertebra. A first interface layer between the first body of porous tantalum metal and the polymeric body includes polyether ether ketone (PEEK) of the polymeric body impregnated into the pores of the first body of porous tantalum metal. A second interface layer between the second body of porous tantalum metal and the polymeric body includes polyether ether ketone (PEEK) of the polymeric body impregnated into the pores of the second body of porous tantalum metal.

Yet another illustrative embodiment is a method of forming a composite interbody vertebral implant. The method includes positioning a first surface of a polymeric body of a polymeric material adjacent a surface of a first body of a porous metal material. The first body of porous metal material is heated to a first elevated temperature and a compressive force is applied between the polymeric body of polymeric material and the first body of porous metal material, causing a portion of the polymeric material to penetrate into pores of the first body of porous metal material. A second surface of the polymeric body of polymeric material is positioned adjacent a surface of a second body of a porous metal material. The second body of porous metal material is heated to a second elevated temperature and a compressive force is applied between the polymeric body of polymeric material and the second body of porous metal material, causing a portion of the polymeric material to penetrate into pores of the second body of porous metal material.

The above summary of some example embodiments is not intended to describe each disclosed embodiment or every implementation of the invention.

BRIEF DESCRIPTION OF THE DRAWINGS

The invention may be more completely understood in consideration of the following detailed description of various embodiments in connection with the accompanying drawings, in which:

FIG. 4 is an alternative embodiment of a composite implant for placement between adjacent vertebrae;

FIG. 4A is a cross-sectional view of the composite implant of FIG. 4 taken along line 4A-4A of FIG. 4;

FIG. 5 is an another alternative embodiment of a composite implant for placement between adjacent vertebrae;

FIG. 5A is a cross-sectional view of the composite implant of FIG. 5 taken along line 5A-5A of FIG. 5;

Figure 1:
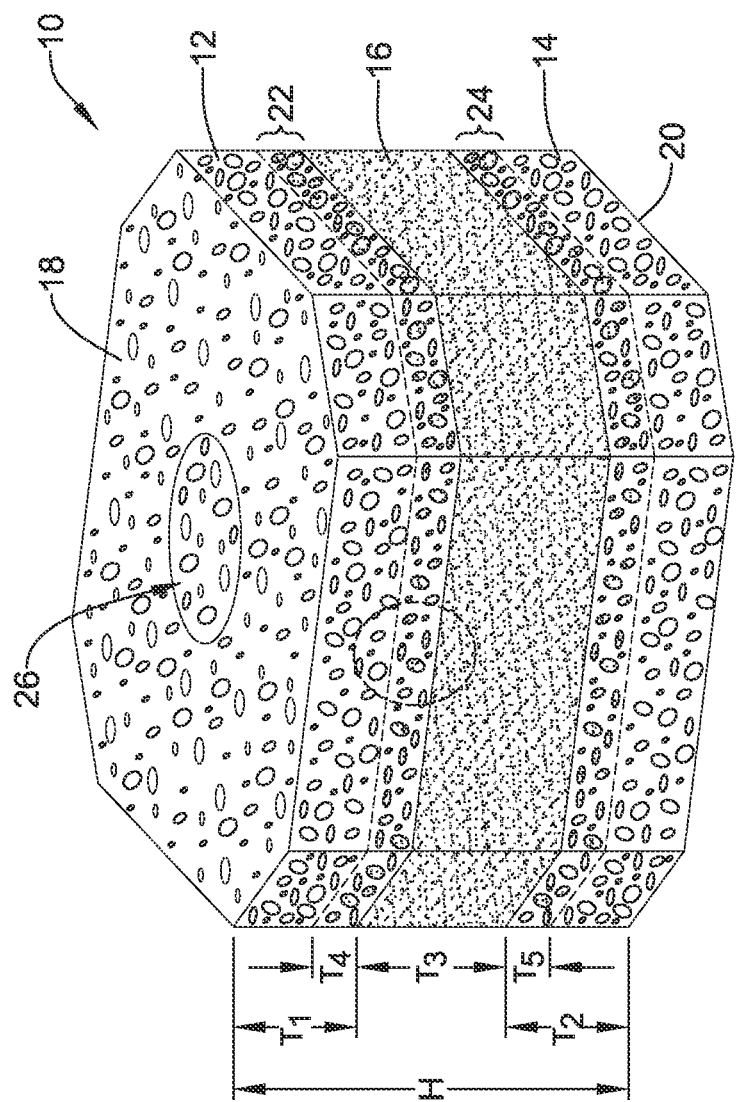
FIG. 1 is a perspective schematic representation of an exemplary composite implant for placement between adjacent vertebrae.

While the invention is amenable to various modifications and alternative forms, specifics thereof have been shown by way of example in the drawings and will be described in detail. It should be understood, however, that the intention is not to limit aspects of the invention to the particular embodiments described. On the contrary, the intention is to cover all modifications, equivalents, and alternatives falling within the spirit and scope of the invention.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (i.e., having the same function or result). In many instances, the term "about" may be indicative as including numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

Although some suitable dimensions, ranges and/or values pertaining to various components, features and/or specifications are disclosed, one of skill in the art, incited by the present disclosure, would understand desired dimensions, ranges and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The detailed description and the drawings, which are not necessarily to scale, depict illustrative embodiments and are not intended to limit the scope of the invention. The illustrative embodiments depicted are intended only as exemplary. Selected features of any illustrative embodiment may be incorporated into an additional embodiment unless clearly stated to the contrary.

Referring now to FIG. 1, there is shown a composite interbody vertebral implant 10 formed of alternating layers of different materials. For instance, the implant may be formed of alternating radioopaque and radiolucent layers, such as metallic layers and polymeric layers bonded together at interfaces between the adjacent layers. In some instances, the metallic layers may be formed of a porous metal defining a plurality of pores formed by a metallic scaffold. As shown in FIG. 1, the implant 10 may include a first body 12 of a porous metal material defining a plurality of pores formed by a metallic scaffold and a second body 14 of a porous metal material defining a plurality of pores formed by a metallic scaffold. For instance, the porous metal material may be tantalum, titanium, zirconium, cobalt, chrome and stainless steel, or alloys thereof. In some instances, the pores of the porous metal will have a pore size of about 150 microns to about 500 microns, or more. However, in other instances a smaller pore size may be desired, such as a pore size of less than about 150 microns. The open cell structure of the porous metal scaffold of the first and second bodies 12, 14 of porous metal may mimic the microstructure of a natural cancellous bone, acting as an osteoconductive matrix for the incorporation of bone, providing optimal permeability and high surface area to encourage new bone in-growth into the pores of the porous metal scaffold of the first and second bodies 12, 14. Furthermore, the porous metal material may have an elastic modulus similar to natural cancellous bone. For instance, depending on its porosity, the porous metal may have an elastic modulus of about 1.5 GPa to about 4 GPa, or about 3 GPa, whereas natural cancellous bone, depending on physiological factors of a specific patient, may have an elastic modulus of about 0.1 GPa to about 3 GPa, or about 0.5 GPa in many instances. In instances in which the first body 12 of porous metal is a superior end plate of the implant 10 defining a superior surface 18 for engagement with an endplate of the vertebral body of a superior vertebra and/or the second body 14 of porous metal is an inferior end plate of the implant 10 defining an inferior surface 20 for engagement with an endplate of the vertebral body of an inferior vertebra, as shown in FIG. 1, the porous metal may provide a roughened surface with a high coefficient of friction against the vertebral bodies of adjacent vertebrae to resist migration of the implant 10 once implanted between the vertebrae.

One exemplary porous metal is Trabecular Metal™ material, which is a porous tantalum material marketed by Zimmer Spine, Inc. of Minneapolis, Minn. This material is also disclosed in several U.S. patents, including, for example, U.S. Pat. Nos. 5,282,861, 5,443,515, and 6,063,442, the disclosures of which are incorporated herein by reference. These patents describe the formation of a tantalum porous structure by chemical vapor deposition of tantalum onto a foam carbon structure.

The implant 10 may also include a polymeric body 16 of a polymeric material, such as a thermoplastic polymeric material, positioned between the first and second bodies 12, 14 of porous metal. Some examples of suitable thermoplastic polymeric materials include polyether ether ketone (PEEK), ultra-high molecular weight polyethylene (UHMWPE), poly(m-ethyl methacrylate) (PMMA), polyethylene terephthalate (PET), and mixtures or blends thereof. Other suitable polymeric materials include thermoplastic elastomers such as polyurethanes and mixtures or blends thereof. Such polymeric materials are radiolucent. In some instances the polymeric material may be chosen such that the polymeric body 16 has an elastic modulus similar to that of natural cancellous bone. For instance, polyether ether ketone (PEEK), which has an elastic modulus of about 3.6 GPa to about 4.1 GPa, or about 4 GPa, may be chosen such that the polymeric body 16 has an elastic modulus similar to that of natural cancellous bone. The polymer material of the polymeric body 16, such as polyether ether ketone (PEEK), may also be chosen based on the similarity of its elastic modulus to the elastic modulus of the porous metal used for the first and second bodies 12, 14. For instance, the elastic modulus of the polymeric body 16 may be within about 3.0 GPa or less, about 2.5 GPa or less, about 2.0 GPa or less, or about 1.0 GPa or less of the elastic modulus of the porous metal scaffold of the first and second bodies 12, 14.

Figure 2:
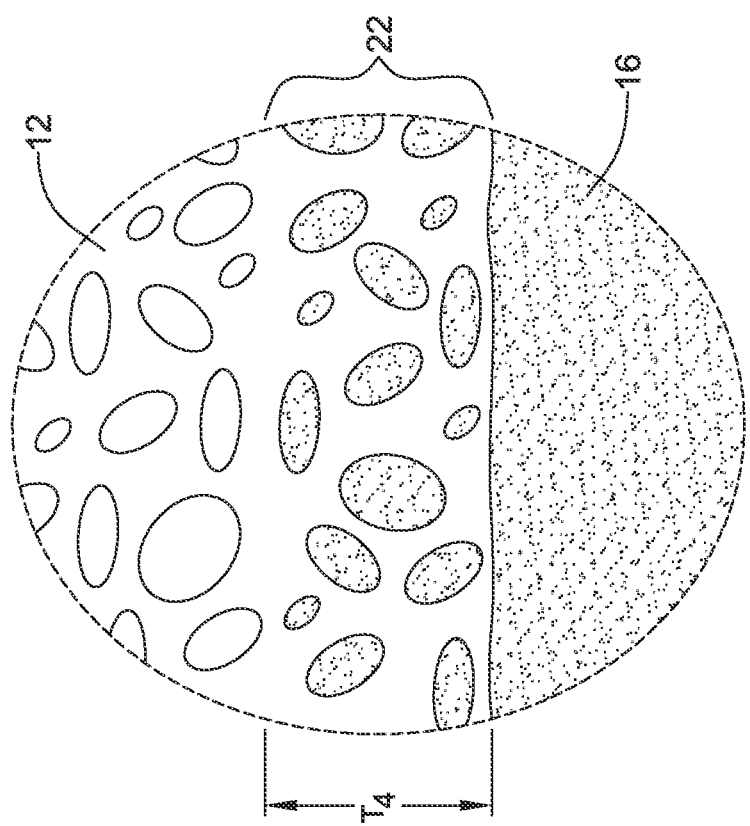
FIG. 2 is an enlarged schematic representation of a portion of the implant of FIG. 1 showing an interface layer bonding two adjacent materials of the composite implant.

As shown in FIG. 1, and further depicted in FIG. 2, during formation of the implant 10, a first interface layer 22 may be formed at the interface between the first body 12 of porous metal and the polymeric body 16 and a second interface layer 24 may be formed at the interface between the second body 14 of porous metal and the polymeric body 16. The first interface layer 22 may include polymeric material of the polymeric body 16 impregnated into the pores of the first body 12 of porous metal. For instance, polymeric material of the polymeric body 16 may infuse or penetrate about 1.0 millimeters or more, about 1.2 millimeters or more, or about 1.5 millimeters or more into the first body 12 of porous metal from the surface of the first body 12 adjacent the polymeric body 16. In other words, the thickness $T_4$ of the first interface layer 22 including both porous metal and polymeric material may be between about 1.0 millimeters to about 2.0 millimeters, about 1.0 millimeters to about 1.5 millimeters, about 1.0 millimeters to about 1.2 millimeters, about 1.0 millimeters, about 1.1 millimeters, about 1.2 millimeters, about 1.3 millimeters, about 1.4 millimeters, or about 1.5 millimeters in some instances.

Similarly, the second interface layer 24 may include polymeric material of the polymeric body 16 impregnated into the pores of the second body 14 of porous metal. For instance, polymeric material of the polymeric body 16 may infuse or penetrate about 1.0 millimeters or more, about 1.2 millimeters or more, or about 1.5 millimeters or more into the second body 14 of porous metal from the surface of the second body 14 adjacent the polymeric body 16. In other words, the thickness $T_5$ of the second interface layer 24 including both porous metal and polymeric material may be between about 1.0 millimeters to about 2.0 millimeters, about 1.0 millimeters to about 1.5 millimeters, about 1.0 millimeters to about 1.2 millimeters, about 1.0 millimeters, about 1.1 millimeters, about 1.2 millimeters, about 1.3 millimeters, about 1.4 millimeters, or about 1.5 millimeters in some instances.

As shown in FIG. 2, polymeric material of the polymeric body 16 may penetrate into and fill pores of the porous metal scaffold of the first and second bodies 12, 14. Infusing polymeric material into the pores of the porous metal scaffold bonds the polymeric body 16 to the first and second bodies 12, 14, joining the components together with a mechanical bond.

The implant 10 may have any desired height H. For instance, the height H of the implant 10 for use in cervical applications may be about 6 millimeters to about 10 millimeters, about 6 millimeters, about 7 millimeters, about 8 millimeters, about 9 millimeters, or about 10 millimeters. If used in other applications, such as thoracic or lumbar applications, the implant 10 may have another desired height H.

The thickness $T_1$ of the first body 12 of porous metal may be about 2 millimeters or more, about 2.5 millimeters or more, or about 3 millimeters or more in some instances. Thus, after formation, about 1.0 millimeters or more, about 1.1 millimeters or more, or about 1.2 millimeters or more of the thickness $T_1$ of the first body 12 may retain open pores for bone in-growth, while the pores of the remainder of the thickness $T_1$ may be filled with polymeric material from the polymeric body 16.

Similarly, the thickness $T_2$ of the second body 14 of porous metal may be about 2 millimeters or more, about 2.5 millimeters or more, or about 3 millimeters or more in some instances. Thus, after formation, about 1.0 millimeters or more, about 1.1 millimeters or more, or about 1.2 millimeters or more of the thickness $T_2$ of the second body 14 may retain open pores for bone in-growth, while the pores of the remainder of the thickness $T_2$ may be filled with polymeric material from the polymeric body 16.

The polymeric body 16 may have a thickness $T_3$ after formation of the implant 10 measured from the lower surface of the first body 12 of porous metal to the upper surface of the second body 14 of porous metal. For instance the thickness $T_3$ of the polymeric body 16 of the implant 10 for use in cervical applications may be about 2 millimeters to about 8 millimeters, about 2 millimeters, about 3 millimeters, about 4 millimeters, about 5 millimeters, about 6 millimeters, about 7 millimeters, or about 8 millimeters. If used in other applications, such as thoracic or lumbar applications, the thickness $T_3$ of the polymeric body 16 of the implant 10 may vary from these dimensions.

It is noted that although the implant 10 is shown as including first and second bodies 12, 14, of porous metal defining the superior and inferior layers or end plates of the implant 10 joined together by the polymeric body 16 positioned between the first and second bodies 12, 14 of porous metal, in other embodiments the implant 10 may include additional layers and/or components, and/or alternative orientations of layers and/or components. For instance, the implant 10 could include three or more bodies of porous metal alternating with two or more bodies of polymeric material in a horizontal or vertical orientation if desired.

The implant 10 may also include a cavity 26 extending into or through the implant 10. As shown in FIG. 1, the cavity 26 may extend through the implant 10 from the superior surface 18 to the inferior surface 20 of the implant 10. In other instances, the cavity 26 may be oriented in a different direction, if desired. The cavity 26 may be configured to be filled with bone growth material prior to implanting the implant 10 between adjacent vertebrae. The bone growth material may facilitate bone growth and fusion between the adjacent vertebrae. In some embodiments, a plurality of cavities 26 may be present to receive bone growth material. The polymeric body 16 may allow post-operative visualization of bone growth or fusion through the implant using radiographic visualization instrumentation.

Figure 3A:
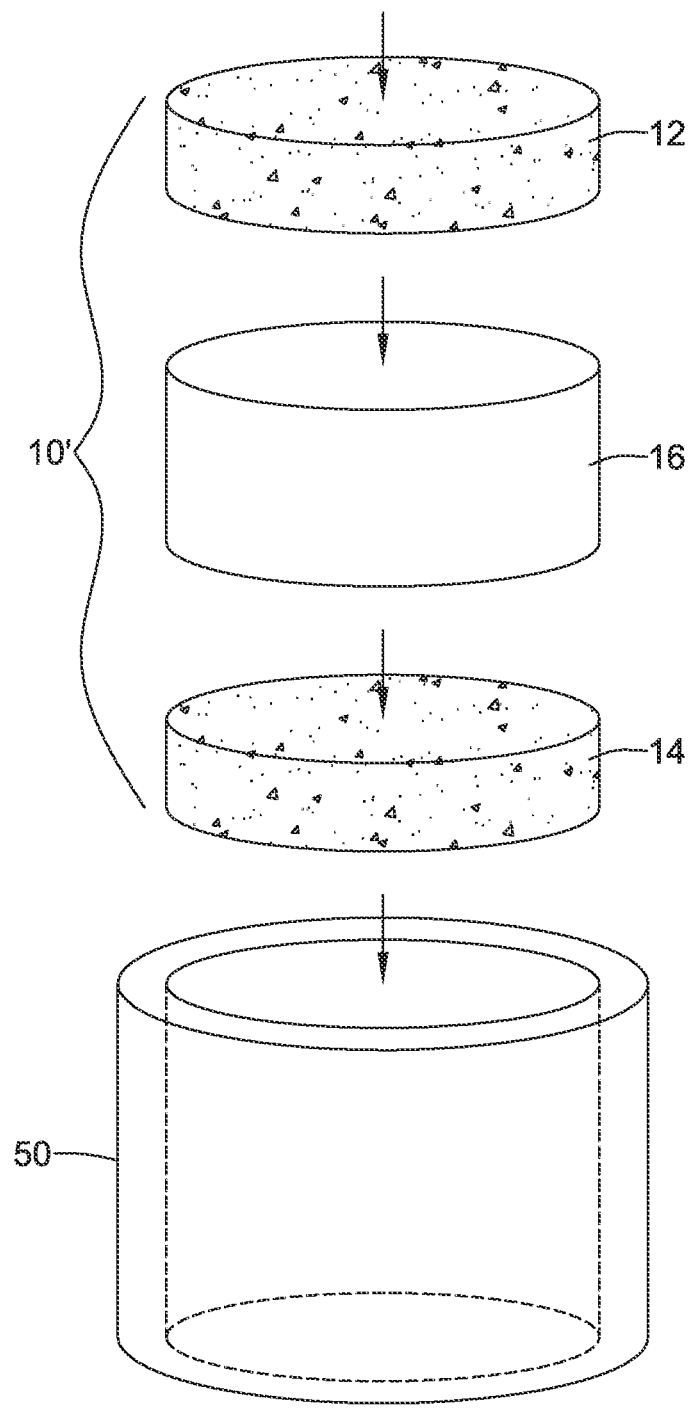
FIGS. 3A through 3E illustrate an exemplary method of forming the composite implant of FIG. 1.

FIGS. 3A through 3E illustrate an exemplary method of forming the implant 10. As shown in FIG. 3A, to form the implant 10, a first body 12 of a porous metal may be placed adjacent to a polymeric body 16 of a polymeric material such that a surface of the first body 12 is adjacent a first surface of the polymeric body 16. Furthermore, a second body 14 of a porous metal may be placed adjacent the polymeric body 16 such that a surface of the second body 14 is adjacent a second surface of the polymeric body 16 opposite the first surface. As shown in FIG. 3A, the first body 12, the second body 14, and the polymeric body 16 may be cylindrically shaped discs in some instances. However, in other instances, the first body 12, the second body 14 and the polymeric body 16 may be of a different shape, if desired.

The pre-bonded assembly 10', or components thereof, may be placed into a mold 50. The mold 50 may be sized such that the periphery of the pre-bonded assembly 10' closely approximates the periphery of the interior of the mold 50. For instance, the interior of the mold 50 may have a diameter sized slightly larger than the diameter of the components of the pre-bonded assembly 10'.

Figure 3B:
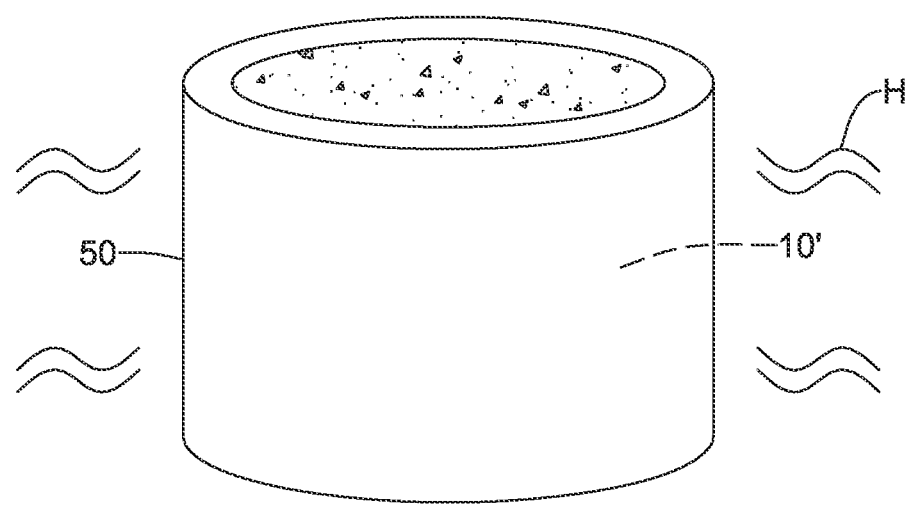

With the pre-bonded assembly 10', or components thereof, positioned in the mold 50, the first body 12 of porous metal and/or the second body 14 of porous metal may be heated by a heat source H to an elevated temperature, shown at FIG. 3B. For example, the first body 12 of porous metal and/or the second body 14 of porous metal may be heated to an elevated temperature in the range of about 60° C. to about 450° C., in the range of about 80° C. to about 400° C., about 140° C. to about 360° C., about 300° C. to about 400° C., about 340° C. to about 400° C., or about 350° C. to about 400° C., in some instances. It is desirable that the elevated temperature be greater than or equal to the glass transition temperature of the polymeric material of the polymeric body 16. In some instances, the elevated temperature may be less than or equal to the melting temperature of the polymeric material of the polymeric body 16. In other instances, the elevated temperature may be greater than or equal to the melting temperature of the polymeric material of the polymeric body 16. The glass transition temperature (Tg) and the melting temperature (Tm) of some suitable polymeric materials are listed in Table 1, below.

TABLE 1

Glass Transition and Melting Temperatures of Some Suitable Polymeric Materials

| | Material | | | |
|---|---|---|---|---|
| | UHMWPE | PMMA | PEEK | PET |
| Tg (° C.) | ~−160 | ~105 | ~143 | ~65 |
| Tm (° C.) | ~135 | — | ~340 | ~260 |

The first body 12 and/or second body 14 may be heated through induction heating. For instance, infrared, radiofrequency, laser or ultra-sound energy from the heating source H may be used to heat the first body 12 of porous metal and/or the second body 14 of porous metal to an elevated temperature in the mold 50. In other instances, the first body 12, the second body 14 and/or the polymeric body 16 may be heated through conduction heating. While other techniques are contemplated, some suitable techniques for bonding the polymeric body 16 to the first body 12 and/or the second body 14 include, but are not limited to, ultrasonic welding, linear vibration welding, orbital vibration welding, spin welding, hot plate welding, laser IRAM welding, etc.

Figure 3C:
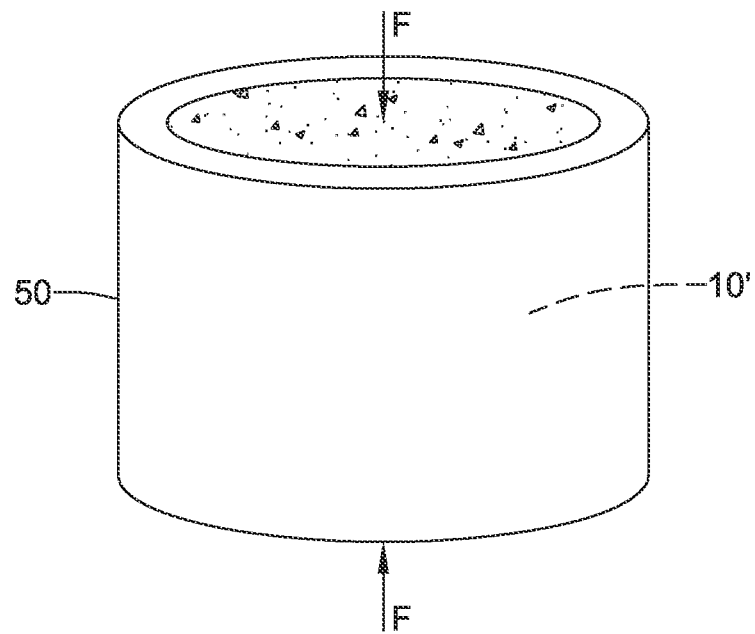

As shown in FIG. 3C, concurrently with and/or subsequent to heating the first body 12 and/or the second body 14, a compressive force F may be applied to the first body 12 and/or the second body 14 to compress the first body 12 against the first surface of the polymeric body 16 and/or to compress the second body 14 against the second surface of the polymeric body 16 in the mold 50. Such a process may be described as a hot-stamping process in which the first body 12 and/or the second body 14 is pressed against the polymeric body 16 while the first body 12 and/or the second body 14 is at an elevated temperature.

As the first body 12 is pressed against the first surface of the polymeric body 16 in the mold 50, the first surface of the polymeric body 16 is heated through conduction heating from the first body 12, softening the polymeric material of the polymeric body 16 proximate the first surface of the polymeric body 16. The compressive force F forces polymeric material at the first surface of the polymeric body 16 into the pores of the porous scaffold of the first body 12, infusing polymeric material into a portion of the first body 12 proximate the polymeric body 16. In some instances, the compressive force F may be between about 1 pound to about 100 pounds of force, between about 1 pound to about 20 pounds of force, about 1 pound to about 5 pounds of force, or about 1 pound to about 2 pounds of force. The force F may be maintained for any desired duration of time. For example, the force F may be maintained for 15 seconds or more, 30 seconds or more, 1 minute or more, or 5 minutes or more in some instances. Pressure applied at the interface between the first body 12 and the polymeric body 16 may be between about 1.25 lb/in$^2$ to about 125 lb/in$^2$, or about 1.25 lb/in$^2$ to about 12.5 lb/in$^2$, or about 1.25 lb/in$^2$ to about 2.5 lb/in$^2$, in some instances. In some instances, the pressure applied may be between 0 psi to about 1000 psi. For instance, the pressure may be about 400 psi or more, about 500 psi or more, about 600 psi or more, about 700 psi or more, about 800 psi or more, or about 900 psi or more.

Similarly, as the second body 14 is pressed against the second surface of the polymeric body 16 in the mold 50, the second surface of the polymeric body 16 is heated through conduction heating from the second body 14, softening the polymeric material of the polymeric body 16 proximate the second surface of the polymeric body 16. The compressive force F forces polymeric material at the second surface of the polymeric body 16 into the pores of the porous scaffold of the second body 14, infusing polymeric material into a portion of the second body 14 proximate the polymeric body 16. In some instances, the compressive force F may be between about 1 pound to about 100 pounds of force, between about 1 pound to about 20 pounds of force, about 1 pound to about 5 pounds of force, or about 1 pound to about 2 pounds of force. The force F may be maintained for any desired duration of time. For example, the force F may be maintained for 15 seconds or more, 30 seconds or more, 1 minute or more, or 5 minutes or more in some instances. Pressure applied at the interface between the second body 14 and the polymeric body 16 may be between about 1.25 lb/in$^2$ to about 125 lb/in$^2$, or about 1.25 lb/in$^2$ to about 12.5 lb/in$^2$, or about 1.25 lb/in$^2$ to about 2.5 lb/in$^2$, in some instances. In some instances, the pressure applied may be between 0 psi to about 1000 psi. For instance, the pressure may be about 400 psi or more, about 500 psi or more, about 600 psi or more, about 700 psi or more, about 800 psi or more, or about 900 psi or more.

Throughout the bonding process, a portion of the polymeric body 16 may be maintained at a temperature below the glass transition temperature of the polymeric material of the polymeric body 16, while the first and second surfaces of the polymeric body 16 adjacent the first and second bodies 12, 14, respectively, are heated to an elevated temperature through conduction heating from the first and second bodies 12, 14. For instance, during the bonding process, the first and second surfaces of the polymeric body 16 may be heated to a temperature greater than or equal to the glass transition temperature of the polymeric material of the polymeric body 16 while a central portion of polymeric body 16 is maintained at a temperature below the glass transition temperature of the polymeric material.

Figure 3D:
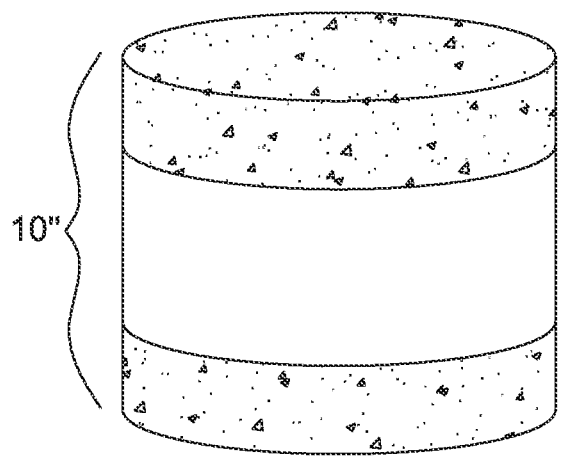
Figure 3E:
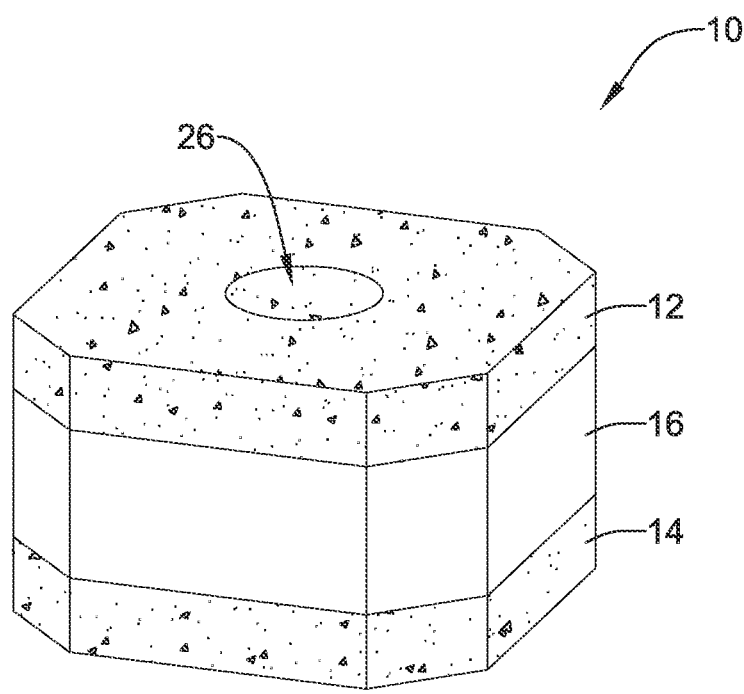

Resultant of the bonding process, a bonded assembly 10'' of the first body 12, the second body 14 and the polymeric body 16 joined together may be formed. The bonded assembly 10'' may then be removed from the mold 50, as shown in FIG. 3D. Subsequently, the bonded assembly 10'' may be shaped into any desired shape such as the shape of the implant 10 shown in FIG. 3E. Various techniques known in the art may be used to shape the bonded assembly 10'' into the final implant 10.

Although it has been illustrated to simultaneously bond the first and second bodies 12, 14 to the polymeric body 16, in some embodiments, the first body 12 may be heated to an elevated temperature and compressed against the first surface of the polymeric body 16 in the mold 50 at one stage of the forming process and the second body 14 may be heated to an elevated temperature and compressed against the second surface of the polymeric body 16 in the mold 50 at a later stage of the forming process.

The implant 10 may be used in a spinal fusion procedure to fuse adjacent vertebrae in order to provide stabilization of the spinal column of a patient suffering from a spinal disorder. For example, after accessing the spinal column of the patient in a percutaneous technique, a minimally invasive technique, an open technique or other technique, a discectomy may be performed to remove at least a portion of a damaged or degenerated intervertebral disc (i.e., spinal disc) between adjacent vertebrae to create a space to insert the implant 10 between the superior vertebra and the inferior vertebra. In one exemplary procedure, a small window is cut in the annulus of the intervertebral disc and portions of the nucleus pulposus is removed through the window to create the space. Once the space has been created, the implant 10 may be inserted into the disc space between the superior vertebra and the inferior vertebra such that the superior surface 18 of the implant 10 contacts the end plate of the vertebral body of the superior vertebra and the inferior surface 20 of the implant 10 contacts the end plate of the vertebral body of the inferior vertebra. Thus, a surface of the first body 12 of porous metal may contact the superior vertebra and a surface of the second body 14 of porous metal may contact the inferior vertebra. The high coefficient of friction between the first body 12 and the end plate of the superior vertebra and the high coefficient of friction between the second body 14 and the end plate of the inferior vertebra due to the roughness of the porous metal may facilitate migration of the implant once installed between the vertebrae. The first and second bodies 12, 14 of porous metal may also allow bone in-growth into the pores of the porous metal from the end plates of the superior and inferior vertebrae, respectively and promote fusion of the adjacent vertebrae.

The first body 12 of porous metal, the second body 14 of porous metal, and the polymeric body 26 may be configured to bear the axial loading from the end plates of the adjacent vertebrae. With the implant 10, the entire axial load between the adjacent vertebra is transferred from the end plate of the superior vertebra to the first body 12 of porous metal, from the first body 12 of porous metal to the polymeric body 16, from the polymeric body 16 to the second body 14 of porous metal, and from the second body 14 of porous metal to the end plate of the inferior vertebra. Thus, the entire axial load between the adjacent vertebrae may be transferred through each of the first body 12 of porous metal, the polymeric body 16, and the second body 14 of porous metal. Thus, the implant 10 may provide load bearing support as well as the proper spacing between the adjacent vertebrae while fusion of the vertebrae takes place.

Prior to being inserted into the disc space created by the removal of intervertebral disc material, the cavity 26 of the implant 10 may be packed or filled with bone growth material to facilitate fusion between the superior and inferior vertebrae in order to immobilize the adjacent vertebrae. Bone growth material may include bone growth inducing material, bone grafting material, or any other type of material that promotes or encourages bone growth or bone fusion.

The presence of the polymeric body 16, formed of a radiolucent material, which at least in part defines the cavity 26, allows medical personnel the ability to assess fusion between the adjacent vertebrae through the fusion implant 10 using a radiographic technique during a post-operative procedure. Thus, the progression and status of the fusion can be monitored and checked post-operatively through the use of a radiographic technique (e.g., x-ray) without the metallic components of the implant 10 obstructing visualization of fusion between the adjacent vertebrae.

Thus, the presence of the first and second bodies 12, 14 of porous metal provide the implant 10 with an osteoconductive scaffold mimicking the trabecular architecture of natural cancellous bone which promotes bone in-growth and migration resistance, while the radiolucency of the polymeric body 16 allows for post-operative visualization through the implant 10 with a radiographic visualization technique to monitor progression and status of fusion between the adjacent vertebrae. Additionally, the materials of each of the first body 12 of porous metal, the second body 14 of porous metal, and the polymeric body 16 may be chosen such that they each have a modulus of elasticity approximating the modulus of elasticity of natural cancellous bone to reduce stress shielding at the fusion site.

Another embodiment of a composite implant 110 is shown in FIGS. 4 and 4A. The implant 110 may be formed of a first body 112 of a porous metal material defining a plurality of pores formed by a metallic scaffold and a second body 114 of a porous metal material defining a plurality of pores formed by a metallic scaffold. The implant 110 may also include a polymeric body 116 of a polymeric material, such as a thermoplastic polymeric material, positioned between the first and second bodies 112, 114 of porous metal.

The first body 112 of porous metal may be of an annular shape located at a superior surface of the implant 110 for contact with the end plate of a superior vertebra in a spinal fusion procedure. The second body 114 of porous metal may be of an annular shape located at an inferior surface of the implant 110 for contact with the end plate of an inferior vertebra in a spinal fusion procedure.

Although not expressly illustrated in the figures, the interface between the first body 112 and the polymeric body 116 may include polymeric material of the polymeric body 116 impregnated into the pores of the first body 112 of porous metal similar to that described above regarding the implant 10. Furthermore, the interface between the second body 114 and the polymeric body 116 may include polymeric material of the polymeric body 116 impregnated into the pores of the second body 114 of porous material similar to that described above regarding the implant 10.

The implant 110 may also include a cavity 126 extending into or through the implant 110. As shown in FIG. 4, the cavity 126 may extend through the implant 110 from the superior surface to the inferior surface of the implant 110. In other instances, the cavity 126 may be oriented in a different direction, if desired. The cavity 126 may be configured to be filled with bone growth material prior to implanting the implant 110 between adjacent vertebrae. The bone growth material may facilitate bone growth and fusion between the adjacent vertebrae. In some embodiments, a plurality of cavities 126 may be present to receive bone growth material. The polymeric body 116 may allow post-operative visualization of bone growth or fusion through the implant using radiographic visualization instrumentation, while the first and second bodies 112, 114 of porous metal may allow bone for in-growth and migration resistance of the implant 110.

The implant 110 may be formed with a process similar to that described above. For example, the implant 110 may be formed by heating the first and second bodies 112, 114 of porous metal to an elevated temperature, such as by induction heating, and pressing the first and second bodies 112, 114 against the polymeric body 116. The surface of the polymeric body 116 against the first and second bodies 112, 114 may be heated and softened through conduction heating by the first and second bodies 112, 114. Polymeric material may thus be impregnated into pores of the first and second bodies 112, 114 of porous metal to bond the first and second bodies 112, 114 to the polymeric body 116, while a portion of the polymeric body 116 is maintained at a temperature less than the glass transition temperature of the polymeric material. The implant 110 may be shaped as desired.

Another embodiment of a composite implant 210 is shown in FIGS. 5 and 5A. The implant 210 may be formed of a first body 212 of a porous metal material defining a plurality of pores formed by a metallic scaffold and a second body 214 of a porous metal material defining a plurality of pores formed by a metallic scaffold. The implant 210 may also include a polymeric body 216 of a polymeric material, such as a thermoplastic polymeric material, positioned between the first and second bodies 212, 214 of porous metal.

The first body 212 of porous metal may be of an annular shape located at a superior surface of the implant 210 for contact with the end plate of a superior vertebra in a spinal fusion procedure. The second body 214 of porous metal may be of an annular shape located at an inferior surface of the implant 210 for contact with the end plate of an inferior vertebra in a spinal fusion procedure.

Although not expressly illustrated in the figures, the interface between the first body 212 and the polymeric body 216 may include polymeric material of the polymeric body 216 impregnated into the pores of the first body 212 of porous metal similar to that described above regarding the implant 10. Furthermore, the interface between the second body 214 and the polymeric body 216 may include polymeric material of the polymeric body 216 impregnated into the pores of the second body 214 of porous material similar to that described above regarding the implant 10.

The implant 210 may also include a cavity 226 extending into or through the implant 210. As shown in FIG. 5, the cavity 226 may extend through the implant 210 from the superior surface to the inferior surface of the implant 210. The annular shape of the first and second bodies 212, 214 may, in part, define the cavity 226 extending through the implant 210. In other instances, the cavity 226 may be oriented in a different direction, if desired. The cavity 226 may be configured to be filled with bone growth material prior to implanting the implant 210 between adjacent vertebrae. The bone growth material may facilitate bone growth and fusion between the adjacent vertebrae. In some embodiments, a plurality of cavities 226 may be present to receive bone growth material. The polymeric body 216 may allow post-operative visualization of bone growth or fusion through the implant using radiographic visualization instrumentation, while the first and second bodies 212, 214 of porous metal may allow bone for in-growth and migration resistance of the implant 210.

The implant 210 may be formed with a process similar to that described above. For example, the implant 210 may be formed by heating the first and second bodies 212, 214 of porous metal to an elevated temperature, such as by induction heating, and pressing the first and second bodies 212, 214 against the polymeric body 216. The surface of the polymeric body 216 against the first and second bodies 212, 214 may be heated and softened through conduction heating by the first and second bodies 212, 214. Polymeric material may thus be impregnated into pores of the first and second bodies 212, 214 of porous metal to bond the first and second bodies 212, 214 to the polymeric body 216, while a portion of the polymeric body 216 is maintained at a temperature less than the glass transition temperature of the polymeric material. The implant 210 may be shaped as desired.

Figure 6A:
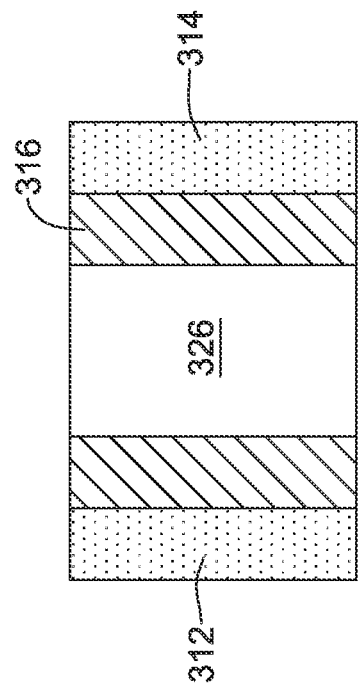
FIG. 6A is a cross-sectional view of the composite implant of FIG. 6 taken along line 6A-6A of FIG. 6.
Figure 6:
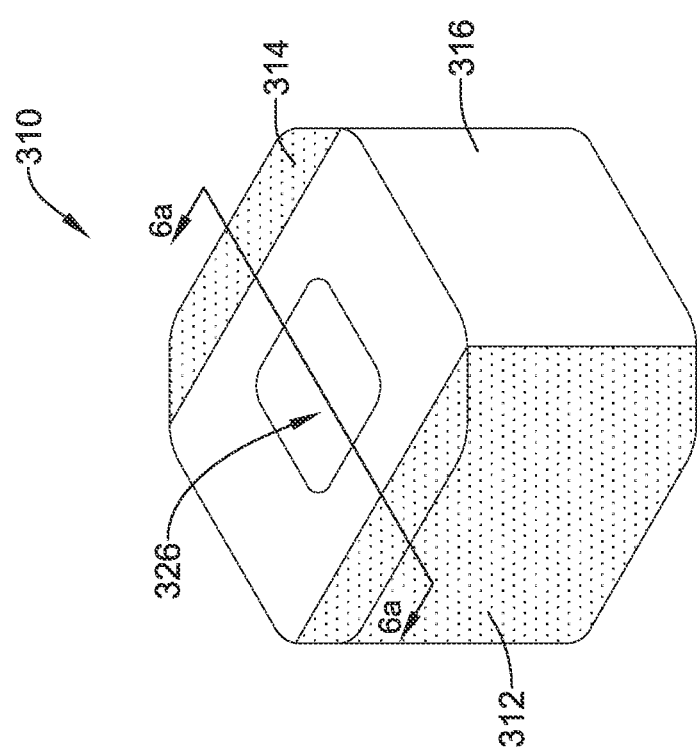
FIG. 6 is yet another alternative embodiment of a composite implant for placement between adjacent vertebrae.

Another embodiment of a composite implant 310 is shown in FIGS. 6 and 6A. The implant 310 may be formed of a first body 312 of a porous metal material defining a plurality of pores formed by a metallic scaffold and a second body 314 of a porous metal material defining a plurality of pores formed by a metallic scaffold. The implant 310 may also include a polymeric body 316 of a polymeric material, such as a thermoplastic polymeric material, positioned between the first and second bodies 312, 314 of porous metal.

The first body 312 of porous metal may extend from the superior surface to the inferior surface along a lateral surface of the implant 310, providing contact with the end plates of superior and inferior vertebrae in a spinal fusion procedure. The second body 314 of porous metal may extend from the superior surface to the inferior surface along a contra-lateral surface of the implant 310, providing contact with the end plates of superior and inferior vertebrae in a spinal fusion procedure.

Although not expressly illustrated in the figures, the interface between the first body 312 and the polymeric body 316 may include polymeric material of the polymeric body 316 impregnated into the pores of the first body 312 of porous metal similar to that described above regarding the implant 10. Furthermore, the interface between the second body 314 and the polymeric body 316 may include polymeric material of the polymeric body 316 impregnated into the pores of the second body 314 of porous material similar to that described above regarding the implant 10.

The implant 310 may also include a cavity 326 extending into or through the implant 310. As shown in FIG. 6, the cavity 326 may extend through the implant 310 from the superior surface to the inferior surface of the implant 310. In other instances, the cavity 326 may be oriented in a different direction, if desired. The cavity 326 may be configured to be filled with bone growth material prior to implanting the implant 310 between adjacent vertebrae. The bone growth material may facilitate bone growth and fusion between the adjacent vertebrae. In some embodiments, a plurality of cavities 326 may be present to receive bone growth material. The polymeric body 316 may allow post-operative visualization of bone growth or fusion through the implant using radiographic visualization instrumentation, while the first and second bodies 312, 314 of porous metal may allow bone for in-growth and migration resistance of the implant 310.

The implant 310 may be formed with a process similar to that described above. For example, the implant 310 may be formed by heating the first and second bodies 312, 314 of porous metal to an elevated temperature, such as by induction heating, and pressing the first and second bodies 312, 314 against the polymeric body 316. The surface of the polymeric body 316 against the first and second bodies 312, 314 may be heated and softened through conduction heating by the first and second bodies 312, 314. Polymeric material may thus be impregnated into pores of the first and second bodies 312, 314 of porous metal to bond the first and second bodies 312, 314 to the polymeric body 316, while a portion of the polymeric body 316 is maintained at a temperature less than the glass transition temperature of the polymeric material. The implant 310 may be shaped as desired.

Figure 7:
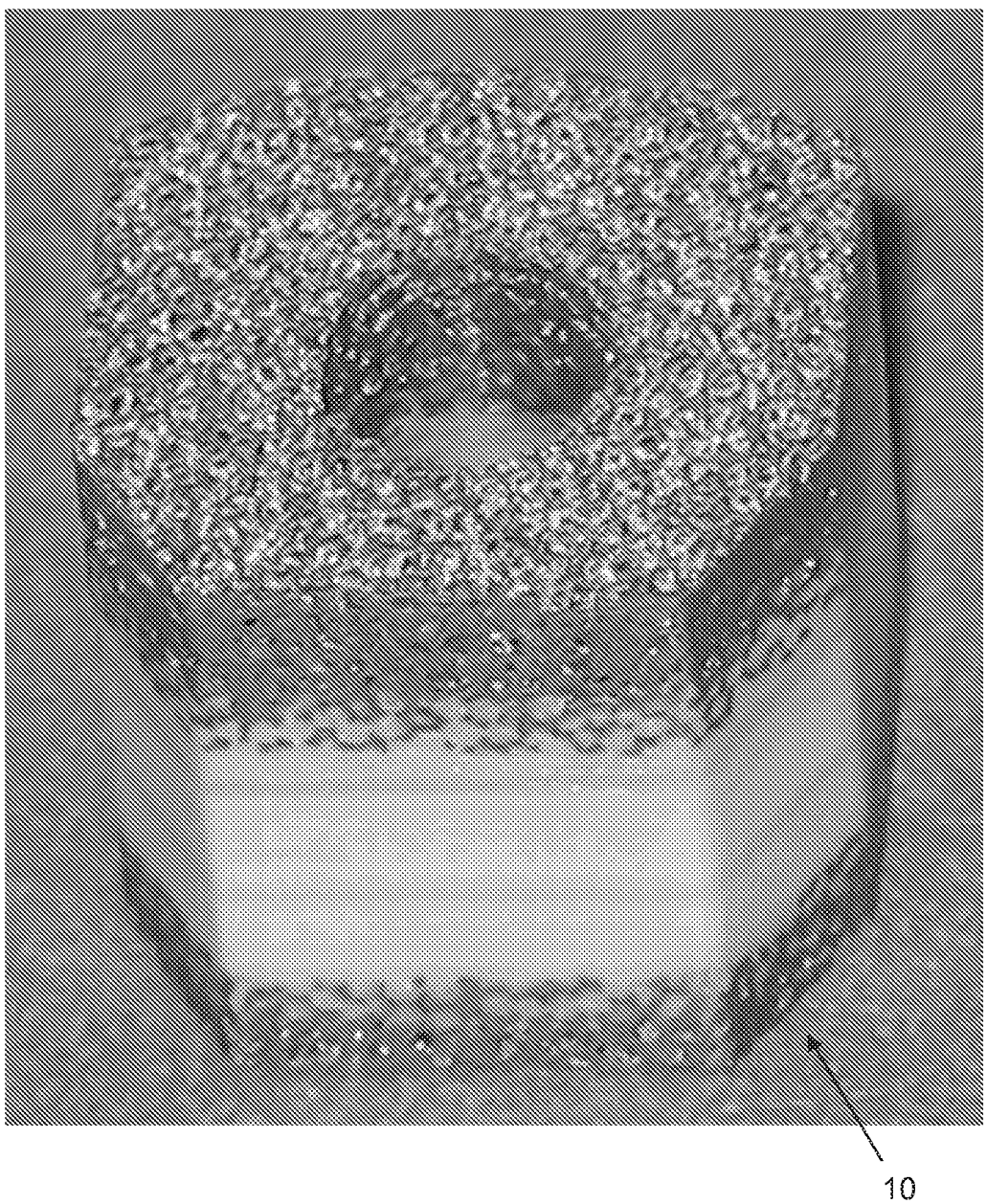
FIG. 7 is an image of a composite implant for use in a spinal fusion.
Figure 8:
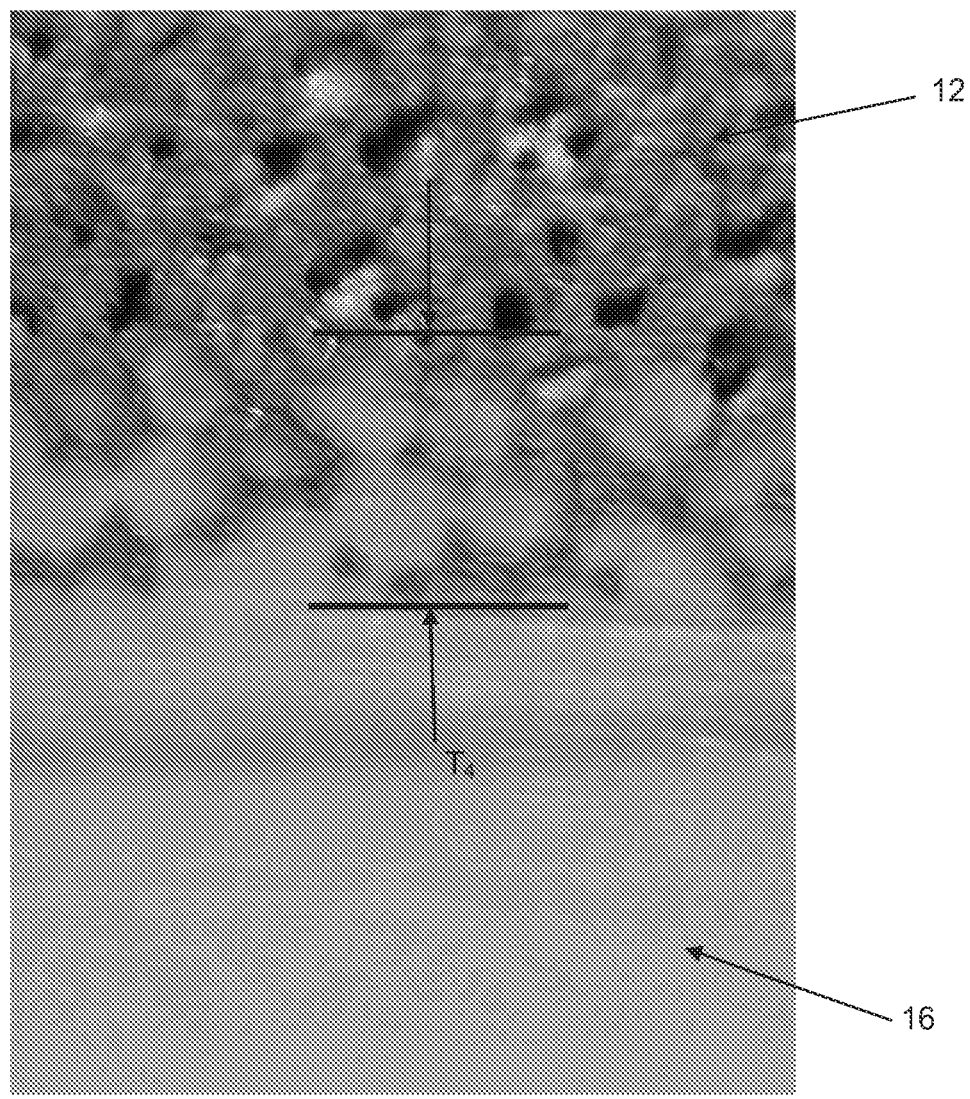
FIG. 8 is an image of an enlarged portion of the composite implant of FIG. 7 showing the interface layer between a porous metal body and a polymeric body of the composite implant.

An image of a composite implant for use in a spinal fusion is shown in FIG. 7. FIG. 8 is an image of an enlarged portion of the composite implant of FIG. 7 showing the interface layer between a porous metal body and a polymeric body of the composite implant. From FIGS. 7 and 8, it can be seen that polymeric material from the polymeric body 16 is impregnated into the pores of the porous metal scaffold of the first and second bodies 12, 14 to mechanically bond the polymeric body 16 between the first and second bodies 12, 14 of porous metal.

It is also contemplated that an interbody implant which is formed entirely of a porous metal material defining a plurality of pores formed by a metallic scaffold, as described herein, may include one or more windows or openings extending entirely through the interbody implant which may aid in allowing post-operative visualization of bone growth or fusion through the implant with an imaging device, such as on an X-ray. Such an implant may be designed to include one or more windows oriented in a superior-inferior orientation, an anterior-posterior orientation, and/or a medial-lateral orientation for visualization purposes. Thus, post-operative visualization in a direction corresponding to the orientation of the window(s) may allow visualization of bone growth through the implant without porous metal material from the implant obstructing the image. Care should be taken to ensure the implant retains sufficient structural integrity to withstand the compressive forces experienced through the spinal column in circumstances in which an implant formed entirely of a porous metal scaffold including windows extending therethrough is used.

Figure 9A:
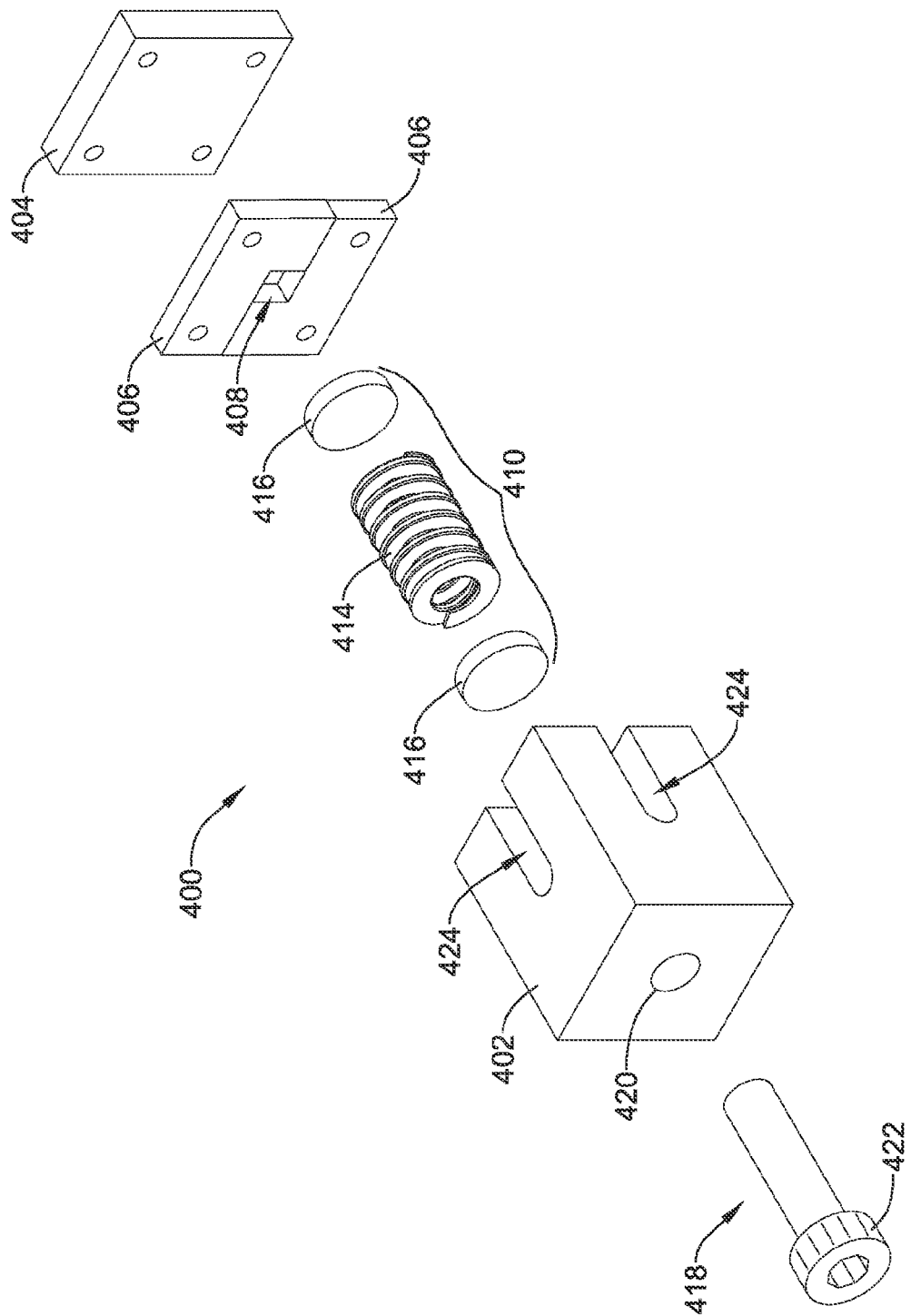
FIGS. 9A and 9B are exploded views of an exemplary fixture forming a composite implant.
Figure 9B:
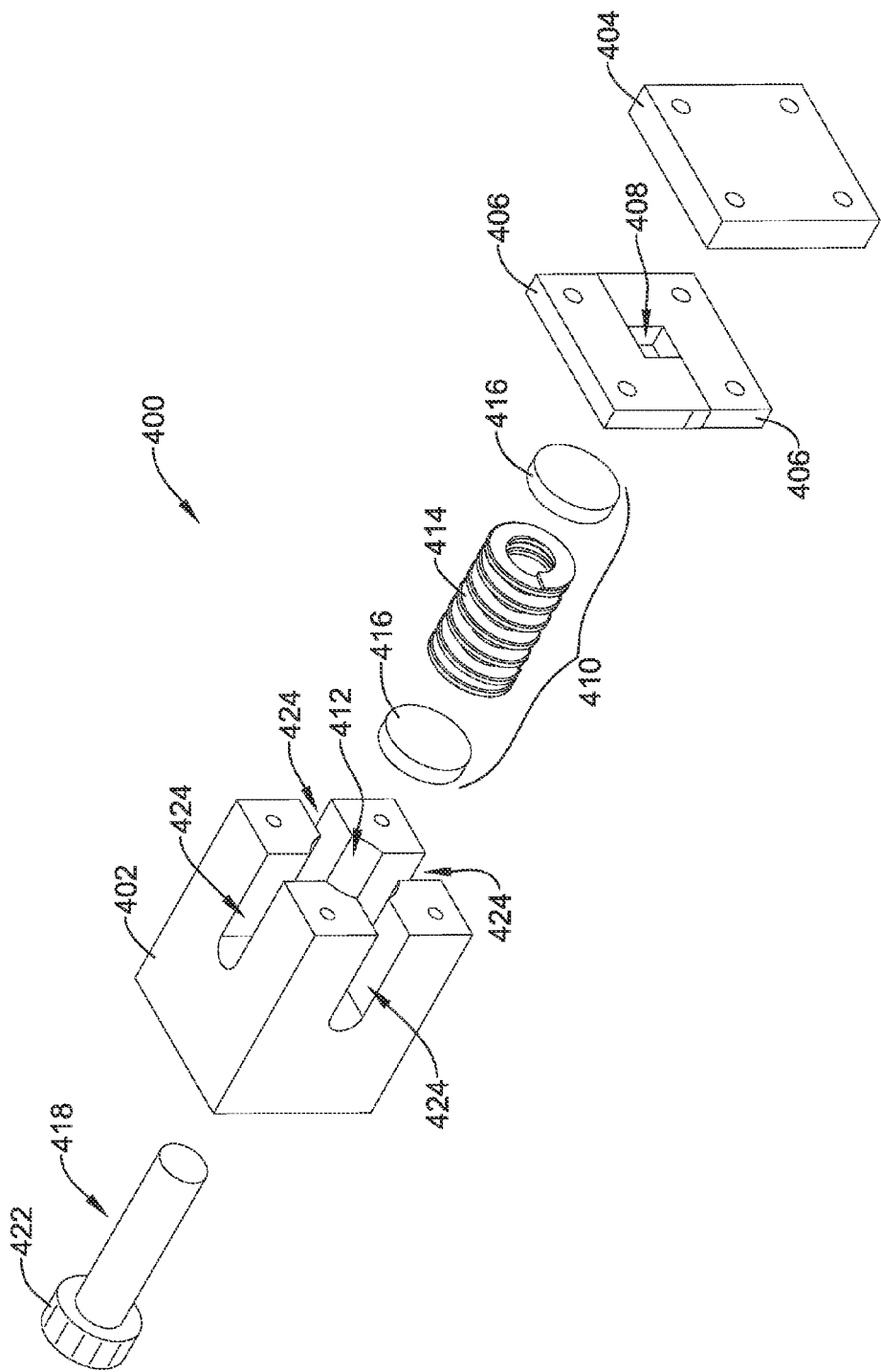

FIGS. 9A and 9B are exploded views illustrating an exemplary embodiment of a fixture 400 configured for forming a composite implant as described herein. The fixture 400 includes an upper block 402, a lower block 404, and one or more, or a plurality of side plates 406. The side plate(s) 406 may be configured to collectively surround components of a composite implant during a molding process. Stated differently, the side plate(s) 406 may define a cavity 408 in which the components of the composite implant are positioned during a molding process. As shown in FIGS. 9A and 9B, the fixture 400 may include two side plates 406 which collectively define the cavity 408. In other embodiments, however, the fixture 400 could include one, three, four, five, six or more side plates 406 arranged to collectively define the cavity 408. The cavity 408 may be any desired shape, such as circular, rectangular, square, oval, etc. The shape and size of the cavity 408 may closely approximate the shape and size of the components of the composite implant to be molded together with the fixture 400. It is noted that various techniques known in the art may be used to shape the bonded assembly of components into the final composite implant subsequent to the molding process, thus the shape of the cavity 408 need not necessarily reflect the shape of the final composite implant, but may in some instances.

The fixture 400 may also include a compression mechanism 410 configured to apply a compressive force to the implant components positioned in the cavity 408. The compression mechanism 410 may be positioned, at least in part, within a bore 412 of the upper block 402. The compression mechanism 410 may include a spring member, such as a helical spring 414 positioned between a pair of spring plungers 416.

The fixture 400 may also include an adjustment mechanism for selectively adjusting the amount of pressure exerted onto the components of the composite implant during the molding process. For example, the fixture 400 may include a threaded screw 418 threadably received in a threaded bore 420 in the upper block 402. The threaded screw 418 may include a head portion or knob 422 which may be manipulated to rotate the screw 418 in the threaded bore 420 to move the screw 418 toward and/or away from the spring 414 in order to adjust the compression of the spring 414, and thus adjust the amount of pressure exerted onto the components of the composite implant.

The upper block 402 may also include one or more, or a plurality of openings 424 extending through the upper block 402 from a perimeter surface of the upper block 402 to the bore 412 in order to visually inspect the compression mechanism 410 and/or visually ascertain the amount of compression of the spring 414 and thus the amount of pressure exerted on the composite implant during the molding process.

When assembled, the side plate(s) 406 may be positioned between the lower block 404 and the upper block 402 with the compression mechanism 410 positioned in the bore 412 of the upper block 402. So arranged, a first plunger 416 of the compression mechanism 410 may be positioned between the spring 414 and the composite implant positioned in the cavity 408, and a second plunger 416 of the compression mechanism 410 may be positioned between the spring 414 and the screw 418. During a molding process, the components of the composite implant may be positioned in the cavity 408 with the composite implant positioned between the lower block 404 and the first plunger 416 of the compression mechanism 410. The upper block 402, lower block 404 and/or side plate(s) 406 may be secured together, for example, with threaded fasteners (not shown) or other fastening means.

During a molding process, compressive forces exerted on the composite implant in the cavity 408 may compress the composite implant between the lower plate 404 and the first plunger 416, while the side plate(s) 406 surround the sides of the composite implant. Accordingly, the spring 414, which is under a desired amount of compression, may push the first plunger 416 against the upper surface of the composite implant while the lower surface of the composite implant is pressed against the lower block 404. The compressive force exerted on the composite implant may be adjusted by rotating the screw 418 in the threaded bore 420 to move the screw 418 toward and/or away from the spring 414. Moving the screw 418 toward the spring 414 shortens or compresses the spring 414, whereas moving the screw 418 away from the spring 414 lengthens or decompresses the spring 414. Thus, adjusting the length of the spring 414 with the screw 418 may adjust the compressive force exerted on the composite implant. In some instances, the pressure applied may be between 0 psi to about 1000 psi. For instance, the pressure may be about 100 psi or more, about 200 psi or more, about 300 psi or more, about 400 psi or more, about 500 psi or more, about 600 psi or more, about 700 psi or more, about 800 psi or more, or about 900 psi or more.

During the molding process, the composite implant may be formed with a process similar to that described above. For example, the composite implant, the components of which are disposed in the cavity 408, may be formed by heating the first and second bodies of porous metal of the composite implant to an elevated temperature, and pressing the first and second bodies against the polymeric body positioned therebetween. The polymeric body, or at least the surfaces of the polymeric body against the first and second bodies of porous metal, may be heated and softened, allowing polymeric material to be impregnated into pores of the first and second bodies of porous metal to bond the first and second bodies to the polymeric body by the compressive forces exerted against the composite implant. When the polymeric body of the composite implant (or portions thereof) is heated to an elevated temperature, the side plate(s) 406 contain the flow of the polymeric material, and thus maintain the shape of the polymeric body. In some instances, a portion of the polymeric body may be maintained at a temperature less than the glass transition temperature of the polymeric material, while portions of the polymeric body adjacent the first and second bodies of porous metal may be heated to a temperature greater than or equal to the glass transition temperature of the polymeric material.

In some instances, the fixture 400, with the components of the composite implant (e.g., first and second bodies of porous metal and the polymeric body) positioned in the cavity 408 and a desired compressive force applied thereto by the compression mechanism 410, may be placed in an oven (not shown), such as a vacuum oven, configured to heat the components of the composite implant to an elevated temperature during the molding process. In some instances, the oven may heat the components of the composite implant through conduction, convection, and/or induction heating.

In some instances, the oven may be purged of air to make the chamber of the oven in which the fixture 400 in placed free of oxygen and/or nitrogen. In some instances, the oven may be filled with an inert gas, such as argon or helium. In some instances, the temperature within the chamber of the oven holding the fixture 400 and composite implant may be increased to an elevated temperature in the range of about 60° C. to about 450° C., in the range of about 80° C. to about 400° C., about 140° C. to about 360° C., about 300° C. to about 400° C., about 340° C. to about 400° C., or about 350° C. to about 400° C., in some instances. It is desirable that the elevated temperature within the oven be greater than or equal to the glass transition temperature of the polymeric material of the polymeric body of the composite implant. In some instances, the elevated temperature may be less than or equal to the melting temperature of the polymeric material of the polymeric body of the composite implant. In other instances, the elevated temperature may be greater than or equal to the melting temperature of the polymeric material of the polymeric body of the composite implant.

While in the oven at the elevated temperature, the compression mechanism 410 of the fixture 400 may apply pressure against the composites of the composite implant. For example, in some instances the compression mechanism 410 may be adjusted to apply a pressure between 0 to about 1000 psi. In some instances, the applied pressure may be about 400 psi or more, about 500 psi or more, about 600 psi or more, about 700 psi or more, about 800 psi or more, or about 900 psi or more. For example, the applied pressure may be in the range of about 500 psi to about 800 psi, in the range of about 600 psi to about 800 psi, or in the range of about 700 psi to about 800 psi in some instances.

The elevated temperature softens the polymeric material which the compressive forces exerted on the porous metal bodies causes polymeric material of the polymeric body to be pushed into the pores of the porous metal bodies, mechanically locking the components together. Subsequent to the molding process, the fixture 400 with the composite implant may be removed from the oven, the composite implant may be removed from the fixture 400, and the composite implant may be shaped as desired.

Those skilled in the art will recognize that the present invention may be manifested in a variety of forms other than the specific embodiments described and contemplated herein. Accordingly, departure in form and detail may be made without departing from the scope and spirit of the present invention as described in the appended claims.

What is claimed is:

1. A composite vertebral implant for positioning between adjacent vertebrae, the composite vertebral implant comprising:
 a polymeric body of a thermoplastic polymeric material positionable between adjacent vertebrae, the polymeric body including an upper surface configured to face a first vertebra and a lower surface configured to face a second vertebra;
 a first porous metallic scaffold member defining a plurality of pores formed therein, the first porous metallic scaffold member having a first surface on a first side of the first porous metallic scaffold member and a second surface on a second side of the first porous metallic scaffold member;
 a second porous metallic scaffold member defining a plurality of pores formed therein, the second porous metallic scaffold member having a first surface on a first side of the second porous metallic scaffold member and a second surface on a second side of the second porous metallic scaffold member;
 wherein a portion of the pores of the first porous metallic scaffold member proximate the first surface of the first porous metallic scaffold member are filled with a portion of the thermoplastic polymeric material of the polymeric body;
 wherein a portion of the pores of the second porous metallic scaffold member proximate the first surface of the second porous metallic scaffold member are filled with a portion of the thermoplastic polymeric material of the polymeric body;
 wherein the second surface of the first porous metallic scaffold member is configured to be positioned against the first vertebra and promote bone in-growth into a portion of the pores of the first metallic scaffold member proximate the second surface of the first porous metallic scaffold member; and
 wherein the second surface of the second porous metallic scaffold member is configured to be positioned against the second vertebra and promote bone in-growth into a portion of the pores of the second metallic scaffold member proximate the second surface of the second porous metallic scaffold member.

2. The composite vertebral implant of claim 1, wherein:
 the composite vertebral implant has a superior surface configured to face the first vertebra and an inferior surface configured to face the second vertebra;

the superior surface of the composite vertebral implant includes the upper surface of the polymeric body and the second surface of the first porous metallic scaffold member; and the inferior surface of the composite vertebral implant includes the lower surface of the polymeric body and the second surface of the second porous metallic scaffold member.

3. The composite vertebral implant of claim 2, further comprising a cavity configured for receiving bone graft material therein, the cavity extending from the superior surface of the composite vertebral implant to the inferior surface of the composite vertebral implant.

4. The composite vertebral implant of claim 1, wherein the first porous metallic scaffold member is a first ring of porous metallic scaffold material having a portion of the polymeric body surrounding a perimeter of the first ring of porous metallic scaffold material.

5. The composite vertebral implant of claim 4, wherein the second porous metallic scaffold member is a second ring of porous metallic scaffold material having a portion of the polymeric body surrounding a perimeter of the second ring of porous metallic scaffold material.

6. The composite vertebral implant of claim 1, wherein the first and second porous metallic scaffold members are formed of a porous metal material having a modulus of elasticity of about 1.5 to about 4 GPa.

7. The composite vertebral implant of claim 6, wherein the polymeric material has a modulus of elasticity within about 3.0 GPa of the modulus of elasticity of the porous metal material.

8. The composite vertebral implant of claim 1, wherein the first and second porous metallic scaffold members are formed of a porous metal material having a modulus of elasticity of about 3 to about 4 GPa and the polymeric material has a modulus of elasticity within about 1 GPa of the modulus of elasticity of the porous metal material.

9. The composite vertebral implant of claim 1, wherein the first and second porous metallic scaffold members are formed of a porous tantalum.

10. The composite vertebral implant of claim 9, wherein the polymeric material is polyether ether ketone (PEEK).

11. A composite vertebral implant for positioning between adjacent vertebrae, the composite vertebral implant comprising:
  a first annular-shaped body of a porous metal material partially defining a superior surface of the composite vertebral implant, the first body of porous metal material defining a plurality of pores formed by a metallic scaffold;
  a second annular-shaped body of a porous metal material partially defining an inferior surface of the composite vertebral implant, the second body of porous metal material defining a plurality of pores formed by a metallic scaffold;
  a polymeric body of a thermoplastic polymeric material positioned between the first annular-shaped body of porous metal material and the second annular-shaped body of porous metal material, the polymeric body having an upper surface partially defining the superior surface of the composite vertebral implant and a lower surface partially defining the inferior surface of the composite vertebral implant; and
  a cavity extending through the composite vertebral implant from the superior surface of the composite vertebral implant to the inferior surface of the composite vertebral implant, the cavity configured to receive bone growth material to facilitate fusion between a first vertebra and a second vertebra.

12. The composite vertebral implant of claim 11, wherein:
  a first interface layer between the first annular-shaped body of porous metal material and the polymeric body includes the polymeric material impregnated into a portion of the pores of the first annular-shaped body of porous metal material; and
  a second interface layer between the second annular-shaped body of porous metal material and the polymeric body includes the polymeric material impregnated into a portion of the pores of the second annular-shaped body of porous metal material.

13. The composite vertebral implant of claim 11, wherein:
  a first portion of the polymeric body surrounds a perimeter of the first annular-shaped body of porous metal material; and
  a second portion of the polymeric body surrounds a perimeter of the second annular-shaped body of porous metal material.

14. The composite vertebral implant of claim 11, wherein the superior surface of the composite vertebral implant is configured to engage the first vertebra and the inferior surface of the composite vertebral implant is configured to engage the second vertebra.

15. The composite vertebral implant of claim 14, wherein:
  a portion of the pores of the first annular-shaped body of porous metal material are configured to allow bone in-growth from the first vertebra; and
  a portion of the pores of the second annular-shaped body of porous metal material are configured to allow bone in-growth from the second vertebra.

16. The composite vertebral implant of claim 11, wherein:
  the upper surface of the polymeric body is co-planar with a superior surface of the first annular-shaped body of porous metal material; and
  the lower surface of the polymeric body is co-planar with an inferior surface of the second annular-shaped body of porous metal material.

17. The composite vertebral implant of claim 11, wherein:
  the porous metal material of the first and second annular-shaped bodies has a modulus of elasticity of about 1.5 to about 4 GPa; and
  the polymeric material has a modulus of elasticity within about 3.0 GPa of the modulus of elasticity of the porous metal material of the first and second annular-shaped bodies.

18. The composite vertebral implant of claim 11, wherein the porous metal material of the first and second annular-shaped bodies has a modulus of elasticity of about 3 to about 4 GPa and the polymeric material has a modulus of elasticity within about 1 GPa of the modulus of elasticity of the porous metal material of the first and second annular-shaped bodies.

19. The composite vertebral implant of claim 11, wherein the porous metal material of the first and second annular-shaped bodies is a porous tantalum.

20. The composite vertebral implant of claim 19, wherein the polymeric material is polyether ether ketone (PEEK).

* * * * *